United States Patent [19]
Sanchez

[11] Patent Number: 5,321,176
[45] Date of Patent: Jun. 14, 1994

[54] HYDROGENATION OF POLYENES

[75] Inventor: Kathryn M. Sanchez, West Chester, Pa.

[73] Assignee: E. I. Du Pont de Nemours and Company, Wilmington, Del.

[21] Appl. No.: 993,476

[22] Filed: Dec. 22, 1992

[51] Int. Cl.$^5$ .................................................. C07C 5/02
[52] U.S. Cl. .................................... 585/277; 585/273; 585/275
[58] Field of Search ................ 585/271, 273, 275, 277

[56] References Cited

U.S. PATENT DOCUMENTS 5,180,870  1/1993  Paciello ............................... 585/277

Primary Examiner—Asok Pal
Assistant Examiner—P. Achutamurthy

[57] ABSTRACT

Hydrogenation of a polyene to a monoene using a ruthenium catalyst that is promoted with water.

4 Claims, No Drawings

HYDROGENATION OF POLYENES

FIELD OF THE INVENTION

This invention relates to the hydrogenation of a polyene to produce a monoene using a ruthenium catalyst that is promoted by water.

BACKGROUND OF THE INVENTION

The hydrogenation of polyenes to produce monoenes using ruthenium complex catalysts is disclosed in Fahey's U.S. Pat. No. 3,925,494. Fahey's U.S. Pat. No. 3,804,914, in Example II shows hydrogenation of polyenes using a ruthenium complex catalyst and excess triphenylphosphine. Fahey discloses in Journal of Organic Chemistry, Vol. 38, No. 1, 1973, pages 80–87 that Lewis Bases, including diethylamine were tested in the hydrogenation of cyclododecatriene. No bases were found to be more effective at enhancing selectivity than triphenylphosphine. No other effects were noted.

The rate of hydrogenation of a particular polyene using a ruthenium catalyst is taught to be increased by adding certain specific amines in an article titled "Selective Homogeneous Hydrogenation of 3-Oxo-1,4-diene Steroids. II. Effects of Basic Additives and para Substituents on the Hydrogenation with Dichlorotris(triphenylphosphine) ruthenium", by Nishimura et al, appearing in Bulletin of the Chemical Society of Japan, Vol. 46, 279–283 (1973).

The process disclosed by the Fahey patents suffers from the difficulty that there is an induction period of considerable length between the time the ingredients of the reaction mixture are combined under reaction conditions, and the time that the mixture actually begins to react at a significant rate.

An object of the present invention is to shorten this induction period.

SUMMARY OF THE INVENTION

The present invention is a process for the hydrogenation of a polyene to a monoene which comprises forming a reaction mixture containing the polyene, hydrogen, a ruthenium-ligand complex hydrogenation catalyst, free triarylphosphine, and water, and reacting the mixture under hydrogenation conditions. The presence of the water promotes the reaction, i.e., it reduces the induction period.

DETAILED DESCRIPTION

It is preferred that the ruthenium-ligand complex hydrogenation catalyst have the formula: $Ru(PAr_3)_2(CO)_2Cl_2$ (in which the triarylphosphine ligand $P(Ar)_3$ is from the group consisting of $P(C_6H_5)_3$, (p-tolyl)$_3$, $P(p-F-C_6H_4)_3$, $P(p-OMe-C_6H_4)_3$ or $P$-(p-F-P $(C_6H_5)_3$).

The process is particularly effective in converting cyclododecatriene to cyclododecene.

The amount of free triarylphosphine present in the reaction mixture should normally be in the range of about 5 to 50 moles per mole of catalyst. Suitable triarylphosphines include: triphenylphosphine, tris-paratolylphosphine, tris-para-fluorophenylphosphine, tris-para-methoxyphenylphosphine. It is desirable that the excess triarylphosphine be the same compound as the phosphine ligand on the ruthenium catalyst.

The amount of catalyst in the reaction mixture may vary widely, but is usually in the range set forth in the Fahey U.S. Pat. No. 3,925,494, i.e., 0.00001 to about 0.5 mole of ruthenium-ligand complex per mole of polyene.

In addition to 1,5,9-cyclododecatriene the process operates on 1,5-cyclooctadiene, and linoleic acid ethyl ester. The Fahey patent '494 indicates that such catalysts are satisfactory for cyclic and acyclic polyenes of up to 20 carbon atoms including 1,3-cyclopentadiene, 1,3-pentadiene, and 1,3,7,9-octa-decatetraene.

The process is normally operated at a pressure in the range of about 100 to about 600 psi and at a temperature in the range of about 130 to about 150° C.

The amount of water in the reaction mixture is preferably in the range of about 0.05 to 10 parts by weight of the reaction mixture.

The reaction can be conducted with or without a solvent Suitable solvents include benzene, toluene, cumene, isooctane, cyclohexane, ethanol, 1-butanol, ethylacetate, tetrahydrofuran and esters or ethers having boiling points higher than 245° C. such as phenyl ether, benzyl benzoate, dioctyl phthalate, benzyl ether and the dimethyl ester of adipic acid.

EXAMPLES

Example 1.

Shaker tube examples demonstrate the effect of added water on the hydrogenation of cyclododecatriene. A blank run was made simultaneously with a run with water added These were run at 500 psig $H_2$, 150° C. for 8 hours Conversion is detined as wt% cyclododecene + wt % cyclododecane.

| Ru* | PPh$_3$ | CDDT** | Water | Conversion |
| --- | --- | --- | --- | --- |
| 0.26 g | 1.80 g | 102 g | 0.00 g | 11.98% |
| 0.26 g | 1.79 g | 105 g | 0.24 g | 85.83% |

*$RuCl_2(CO)_2(PPh_3)_2$
**Cyclododecatriene

Example 2

Example 1 was repeated. The results in the following table show conversion after 4 hours of reaction.

| Ru* | PPh$_3$ | CDDT** | Water | Conversion |
| --- | --- | --- | --- | --- |
| 0.26 g | 1.86 g | 135 g | 0.00 g | 33.16% |
| 0.25 g | 1.80 g | 135 g | 0.50 g | 98.40% |

*$RuCl_2(CO)_2(PPh_3)_2$
**Cyclododecatriene

I claim:

1. A process for the hydrogenation of a polyene to a monoene which comprises forming a reaction mixture containing (a) the polyene, (b) hydrogen, (c) a ruthenium-ligand complex hydrogenation catalyst $Ru(PAr_3)_2(CO)_2Cl_2$ in which the triarylphosphine ligand $P(Ar)_3$ is selected from the group consisting of P(p-tolyl)$_3$P(p-F-C$_6$H$_4$)$_3$, P(p-OMe-C$_6$H$_r$)$_3$ and P(C$_6$H$_5$)$_3$, (d) free triarylphosphine and (e) water, and reacting the mixture under hydrogenation conditions.

2. The process of claim 1 in which the polyene is cyclododecatriene and the monoene is cyclododecene.

3. The process of claim 2 in which the amount of water in the mixture is in the range of about 0.05 to about 10 part by weight of the reaction mixture 4. The process of claim 1 in which a solvent is present in the reaction mixture.

* * * * *